US008929970B2

(12) United States Patent
Wollin

(10) Patent No.: US 8,929,970 B2
(45) Date of Patent: *Jan. 6, 2015

(54) APPARATUS AND METHOD FOR MAGNETIC RESONANCE MEASUREMENT AND MAPPING OF ELECTRICAL IMPEDANCE, COMPLEX PERMITTIVITY AND COMPLEX CONDUCTIVITY AS APPLIED TO DETECTION AND EVALUATION OF SAMPLE PATHOLOGY

(75) Inventor: Ernest Wollin, Sarasota, FL (US)

(73) Assignee: Wollin Ventures, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/472,084

(22) Filed: May 15, 2012

(65) Prior Publication Data

US 2012/0223712 A1  Sep. 6, 2012

Related U.S. Application Data

(63) Continuation of application No. 10/902,263, filed on Jul. 30, 2004, now Pat. No. 8,200,309, which is a continuation-in-part of application No. PCT/US03/27122, filed on Aug. 29, 2003.

(60) Provisional application No. 60/406,924, filed on Aug. 30, 2002.

(51) Int. Cl.
*A61B 5/05* (2006.01)
*G01R 33/48* (2006.01)
*G01R 33/28* (2006.01)

(52) U.S. Cl.
CPC ............ *G01R 33/28* (2013.01); *G01R 33/4808* (2013.01)
USPC .......................................... 600/407

(58) Field of Classification Search
USPC ......... 600/407, 410–411, 415, 421–422, 425, 600/427, 547; 324/307, 309
See application file for complete search history.

(56) References Cited

U.S. PATENT DOCUMENTS

| 3,324,848 A | 6/1967 | Domeier et al. |
| 4,608,991 A | 9/1986 | Rollwitz |

(Continued)

FOREIGN PATENT DOCUMENTS

| EP | 0 631 151 B1 | 12/1994 |
| WO | WO-01/36919 A1 | 5/2001 |
| WO | WO-2004/019763 A2 | 3/2004 |

OTHER PUBLICATIONS

A. D. Poularikas (ed.), "The Transforms and Applications Handbook," 1996, pp. 221-222, CRC Press.

(Continued)

*Primary Examiner* — Rene Towa
(74) *Attorney, Agent, or Firm* — Foley & Lardner LLP

(57) ABSTRACT

A method of measurement of or mapping the distribution of complex permittivity, complex conductivity, complex impedance, or electric loss angle during magnetic resonance imaging or analysis. The method includes applying a time-varying electric field of a Faraday shield to a sample and cross-correlating the line spectrum signal so produced with the voltage applied to the Faraday shield in a detection circuit. The method permits non-contrast magnetic resonance screening for breast cancer in vivo and/or continuous measurement of electrical characteristics of materials at variable frequencies in vitro. A system of detecting and evaluating sample pathology includes a Faraday shield device that includes parallel electrodes oriented orthogonal to the static magnetic field of a MRI device to produce a time varying electric field. A detector is coupled to the MRI device to detect at least one of a complex permittivity, a complex conductivity, and an electrical impedance of the sample.

23 Claims, 6 Drawing Sheets

(56) References Cited

U.S. PATENT DOCUMENTS

| | | | |
|---|---|---|---|
| 4,758,789 | A | 7/1988 | Ono et al. |
| 5,270,656 | A | 12/1993 | Roberts et al. |
| 5,363,845 | A | 11/1994 | Chowdhury et al. |
| 5,412,322 | A | 5/1995 | Wollin |
| 5,755,667 | A | 5/1998 | Friedrich |
| 5,757,187 | A | 5/1998 | Wollin |
| 5,782,763 | A | 7/1998 | Bianco et al. |
| 5,810,742 | A | 9/1998 | Pearlman |
| 6,166,540 | A | 12/2000 | Wollin |
| 6,167,300 | A | 12/2000 | Cherepenin et al. |
| 6,236,886 | B1 | 5/2001 | Cherepenin et al. |
| 6,342,784 | B1 | 1/2002 | Wollin |
| 6,397,095 | B1 | 5/2002 | Eyuboglu et al. |
| 6,452,390 | B1 | 9/2002 | Wollin |
| 6,545,471 | B2 | 4/2003 | Wollin |
| 7,603,158 | B2 | 10/2009 | Nachman et al. |
| 2003/0081370 | A1 | 5/2003 | Haskell et al. |
| 2003/0093005 | A1 | 5/2003 | Tucker |
| 2003/0160024 | A1 | 8/2003 | Kawaguchi et al. |
| 2004/0077944 | A1 | 4/2004 | Steinberg et al. |

OTHER PUBLICATIONS

Assenheimer, M., et al., "The T-SCAN™ technology: electrical impedance as a diagnostic tool for breast cancer detection", Physiol. Meas., vol. 22, pp. 1-8 (2001).

C. A. Balanis, "Advanced Engineering Electromagnetics," 1989, Section 2.8, pp. 72-103, John Wiley & Sons.

Esserman, L., et al., "Utility of magnetic resonance imaging in the management of breast cancer: Evidence for improved preoperative staging", J. Slin. Oncol., vol. 17, pp. 110-119 (1999).

G.C. Scott et al., "Measurement of Nonuniform Current Density by Magnetic Resonance," IEEE Trans. On Medical Imaging, Sep. 1991, vol. 10, No. 3, pp. 362-374.

Harms, S.E., et al., "Breast MRI", J. Clin. Imag., vol. 25, pp. 227-246 (2001).

Hayes, "Electrical Impedance Images for Breast Gain FDA Approval," Diagnostic Imaging (Jun. 1999), vol. 21, No. 6, pp. 19-20.

Kaiser, W. A., "False-positive results in dynamic MR mammography. Causes, frequency and methods to avoid.", Magn. Reson, Imaging Clin. N. Am., vol. 2, No. 4, pp. 539-555 (1994).

Kaiser, W. A., et al., "MR imaging of the breast: fast imaging sequences with and without Gd-DTPA" Preliminary observations, Radiology, vol. 170, No. 3, pt. 1, pp. 681-686 (1989).

M. Holz et al., "NMR Measurements of Internal Magnetic Field Gradients Caused by the Presence of an Electric Current in Electrolyte Solutions," Journal of Magnetic Resonance, 1980, vol. 40, pp. 595-599.

Malich, A., et al., "Differentiation of mammographically suspicious lesions: Evaluation of breast ultrasound, MRI mammography, and electrical impedance scanning as adjunction technologies in breast cancer detection", Clin. Radiology, vol. 56, pp. 278-283 (2001).

Malich, A., et al., "Electrical impedance scanning as a new imaging modality in breast cancer detection—a short review of clinical value on breast application, limitations, and perspective", Nucl. Instr. Methods Phys. Res., vol. A497, pp. 75-81 (2003).

Oh et al., "Electrical Conductivity Imaging by Magnetic Resonance Electrical Impedance Tomography (MREIT)," Magnetic Resonance in Medicine (2003), vol. 50, pp. 875-878.

S.A. Mirowitz et al., "Breast MR Imaging." Magnetic Resonance Imaging Clinics of North America, May 2001, vol. 9, No. 2, 185 pages.

Schelfout, K., et al., "Contract-enhanced MR Imaging of breast lesions and effect on treatment", Eur. J. Surg. Oncol., vol. 30, No. 5, pp. 501-507 (2004).

Surowiec, A. J., "Dielectric properties of breast carcinoma and the surrounding tissues", IEEE Trans. Biomed. Eng., vol. 35, No. 4, pp. 257-263 (1988).

APPARATUS AND METHOD FOR MAGNETIC RESONANCE MEASUREMENT AND MAPPING OF ELECTRICAL IMPEDANCE, COMPLEX PERMITTIVITY AND COMPLEX CONDUCTIVITY AS APPLIED TO DETECTION AND EVALUATION OF SAMPLE PATHOLOGY

RELATED APPLICATIONS

This application is a continuation of U.S. patent application Ser. No. 10/902,263, filed Jul. 30, 2004, now U.S. Pat. No. 8,200,309 granted Jun. 12, 2012; which is a continuation-in-part of PCT Application No. PCT/US03/27122, filed on Aug. 29, 2003; which claims the benefit of Provisional Application No. 60/406,924, filed on Aug. 30, 2002, all of which are incorporated by reference herein in their entirety.

BACKGROUND OF THE INVENTION

This invention generally relates to magnetic resonance and more particularly to the measurement of electrical impedance, complex permittivity, and/or complex conductivity by the application of time-varying electric fields in an imaging volume (especially as it enables detection and evaluation of sample, e.g., human breast, pathology) or in a homogeneous sample volume (especially as it relates to industrial materials testing).

Magnetic resonance imaging of the human breast with and without gadolinium enhancement is a standard procedure in clinical medicine. S. A. Mirowitz et al., "Magnetic Resonance Imaging Clinics of North America," W.B. Saunders Co., vol. 9, no. 2 (May 2001). Current techniques generally utilize the injection of e.g., gadolinium contrasting agents for breast imaging. The dielectric properties of breast carcinoma have been extensively investigated in vitro. A. J. Suroweic, et al., "Dielectric Properties of Breast Carcinoma and Surrounding Tissues," IEEE Trans. On Biomedical Engineering, vol. 35, no. 4, pp. 257-263 (April 1988). Electrical impedance imaging in vivo is an FDA approved method for breast cancer detection. J. C. Hayes, "Electrical impedance images for breast gain FDA approval," Diagnostic Imaging, pp. 19-20 (June 1999). U.S. Pat. Nos. 5,412,322, 5,757,187, 6,166,540 and 6,342,784 (incorporated by reference herein for all purposes) describe various effects produced by superposition of time varying electric fields in magnetic resonance devices. The production of gradients by an electric conduction current and the measurement of non-uniform conduction current density by magnetic resonance are described in the prior art. Holz, M. et. al., "NMR Measurements of Internal Magnetic Field Gradients Caused by the Presence of an Electric Current in Electrolyte Solutions," Journal of Magnetic Resonance, vol. 40, pp. 595-599 (1980); G. C. Scott, et al., "Measurement of Nonuniform Current Density by Magnetic Resonance," IEEE Trans. On Medical Imaging, vol. 10, no. 3, pp. 362-374, (September 1991). Complex permittivity is reviewed in other prior art. C. A. Balanis, "Advanced Engineering Electromagnetics," Wiley & Sons, Section 2.8, (1989). Further background information can be found in other art. "The Transforms and Applications Handbook," A. D. Poularikas (ed.), CRC Press, pp. 221-222 (1996).

SUMMARY OF THE INVENTION

The present invention provides a method for large population screening for breast cancer without the use of ionizing radiation or the parenteral administration of medications. It also provides a method for continuously measuring the dielectric properties of materials in a manufacturing process at variable frequencies.

An object of this invention is to provide a non-invasive, non-contrast, non-ionizing radiation imaging method for screening a sample for cancer by providing an attachment to existing magnetic resonance imaging ("MRI") machines. By non-contrast, it is meant that injection of a contrast agent (e.g., Gadolinium compounds) is not required (but still could be used). It is possible, however, to use a contrast agent. An additional object of this invention is to provide a method for measuring the electrical impedance, complex permittivity, and/or complex conductivity of a homogeneous sample in a materials testing or production control application by providing an attachment to existing magnetic resonance analysis machines.

According to one embodiment of the present invention, a method of detecting and evaluating spatially distributed sample pathology may include placing a sample to be measured in a magnetic resonance imaging device, providing a Faraday shield device having an electrode array, applying a potential distribution to the Faraday shield device which produces a time varying electric field $\vec{E}$ in the sample, which creates a spatially distributed current field $\vec{J}$, which generates time varying focal periodic aberrations in the local magnetic field $\vec{b}_0$ that periodically vary the phase of spins within the sample, and measuring or mapping at least one of complex permittivity, complex conductivity, and electrical impedance of the sample. This embodiment is applicable to, e.g., spatially ordered anatomic and pathological analysis of sample pathology utilizing a conventional magnetic resonance imaging device with a detection circuit attachment. In another aspect, the method may further comprise measuring the complex permittivity at a phase modulating frequency of the time varying potential distribution.

According to another embodiment of the present invention, a method of detecting and evaluating sample spatially ordered pathology may comprise: placing a human breast to be measured in a Faraday shield device having electrodes; applying to the Faraday shield device a time varying potential having a phase modulating frequency, which creates a time varying electric field $\vec{E}$ in the breast, which creates a time varying current field in the breast, which periodically varies a phase of spins within the breast; and measuring a complex permittivity distribution of the breast at the phase modulating frequency.

According to another embodiment of the present invention, a method of measuring dielectric properties by the application of time-varying electric fields in a sample may include placing the sample in a magnetic resonance device, providing a Faraday shield device, and applying a potential distribution V to the Faraday shield device, which generates a time varying electric field $\vec{E}$ in the sample, which creates a time varying current field $\vec{J}$ in the sample, which creates/generates a periodic magnetic field $\vec{b}_0$ that periodically varies the phase of spins within the sample, and measuring at least one of complex permittivity, complex conductivity, and electrical impedance of the sample with a detection circuit attachment. This embodiment is applicable to continuous measurement of dielectric properties at a controllable frequency $\Omega$.

According to another embodiment of the present invention, a system of detecting and evaluating spatially distributed sample pathology may include a magnetic resonance imaging device to produce an image of a sample (the magnetic resonance imaging device generating a static magnetic field $\vec{B}_0$ and gradient fields $\vec{G}$, a radio frequency generator operating near the Larmor frequency $\omega_0$ and including receiving coils and transmitting coils or transmitter-receiver coils). The system further includes a Faraday shield that includes parallel electrodes oriented orthogonal to the static magnetic field to produce a time varying electric field in the sample. A voltage source may also be provided and adapted to apply a periodic voltage V at a frequency $\Omega$ to the Faraday shield device. A detector may also be provided to detect one of a complex permittivity, a complex conductivity, and an electrical impedance of the sample.

According to a preferred aspect of the present invention, the sample may be a human breast. The Faraday shield device may comprise a pair of compression paddles and the electrodes may be oriented in parallel to each other. The electrodes may be embedded in an insulating material. The insulating material may have a high dielectric constant and may comprise one or more ferroelectric materials. According to another preferred aspect of the present invention, the electrodes may be further oriented substantially perpendicular to the main magnetic field $B_0$ of the magnetic resonance imaging device.

According to another preferred aspect of the present invention, the Faraday shield device may comprise a pair of compression paddles, and the method may further comprise: placing the Faraday shield within an imaging region of the magnetic resonance imaging device; and placing one of the receiver coil and the transmitter-receiver coil of the magnetic resonance imaging device near the compression paddles.

According to another preferred aspect of the present invention, the method may further comprise detecting orthogonal components of each sideband of a line spectrum resolved with respect to the phase of a voltage applied to the Faraday shield device. The method may further comprise determining a ratio of the resolved real and imaginary components of the sidebands. The method may further comprise determining an electric loss angle of the sample. The method may further comprise detecting orthogonal components of each sideband of a line spectrum resolved with respect to the phase of a voltage applied to the Faraday shield device at a frequency $\Omega<<$(or much less than) $\omega_0$, the Larmor frequency of the magnetic resonance imaging device. The method may further comprise identifying focal aberrations contained in an image produced by the magnetic resonance imaging device.

According to another embodiment of the present invention, a method of measuring electrical impedance by the application of time-varying electric fields in an imaging volume may comprise: placing a sample in a magnetic resonance device; providing a detector to the magnetic resonance device; providing a Faraday shield device about the sample, where the Faraday shield device may include electrodes oriented parallel to each other; applying a periodic potential distribution across the Faraday shield device to create a time varying electric field in the sample, which creates a local time varying current field in the sample, wherein the local time varying current field creates a periodic aberration in a local magnetic field that periodically varies a phase of spins within the sample; and measuring an electrical impedance of the sample with the detector.

According to another embodiment of the present invention, a system of detecting and evaluating sample pathology may comprise: a magnetic resonance imaging device to produce an image of a sample, the magnetic resonance imaging device generating a static magnetic field and including one of receiving coils and transmitter-receiver coils; a Faraday shield device that includes parallel electrodes oriented orthogonal to the static magnetic field connected to a voltage source adapted to generate a periodic voltage V at a frequency $\Omega$; and a detector to detect one of a complex permittivity, a complex conductivity, and an electrical impedance of the sample.

In a preferred aspect of the present invention, the detector may comprise: first demodulators supplied with a quadrature output at a Larmor frequency $\omega_0'$ from a magnetic resonance master radio frequency oscillator; a first amplifier to sum first output signals from the first demodulators; a second amplifier to receive a second output signal from the summing amplifier; and second demodulators coupled to the second amplifier to provide cross-correlated outputs corresponding to at least one of real and imaginary components that correspond to a signal received by the one of receiver and transmitter-receiver coils from a location x in the sample, and corresponding to the frequency $\omega_0'$ resolved with respect to a phase of V. The second demodulators may comprise a series n of double-balanced demodulator pairs, each double balanced demodulator pair coupled to the second amplifier, to provide cross-correlated outputs corresponding to real and/or imaginary components of the signal received by the one of receiver coils and transmitter-receiver coils from the location x in the sample. The second demodulators may be supplied with frequency sources sin (n$\Omega$t) and cos (n$\Omega$t).

In another preferred aspect of the present invention, the system may further comprise a processor to analyze the cross-correlated outputs of the second demodulators and to provide the complex permittivity at the location x at frequency $\Omega$. The Faraday shield may include a pair of non-conductive compression paddles, each compression paddle comprising an electrode array contained in an insulating portion thereof and coupled to the voltage source. At least one of receiving coils and transmitter-receiver coils may be disposed near at least one of the compression paddles. In another preferred aspect of the present invention, the periodic voltage may be either continuously applied or pulsed.

According to another embodiment of the present invention, a system for measuring the electrical impedance of a sample may comprise: a magnetic resonance device; a Faraday shield device disposed about the sample, where the Faraday shield device may include a pair of electrode arrays oriented substantially parallel to each other and substantially orthogonal to the static magnetic field of the magnetic resonance device; a voltage source to apply a periodic potential distribution across the Faraday shield device to create a time varying electric field in the sample, which creates a local time varying current field in the sample, which creates a periodic aberration in a local magnetic field that periodically varies a phase of spins within the sample; and a detector coupled to the magnetic resonance device to measure a value corresponding to an electrical impedance of the sample.

Further features and advantages of the invention, as well as the structure and operation of various embodiments of the invention, are described in detail below with reference to the accompanying drawings.

BRIEF DESCRIPTION OF THE DRAWINGS

The accompanying drawings, which are incorporated in, and form a part of, the specification, illustrate some embodiments of the present invention and, together with the description, serve to explain the principles of the invention. In the drawings:

FIG. 8B shows an image of the same breast with the Faraday shield voltage V turned on.

DESCRIPTION OF THE EXEMPLARY EMBODIMENTS

Figure 1:
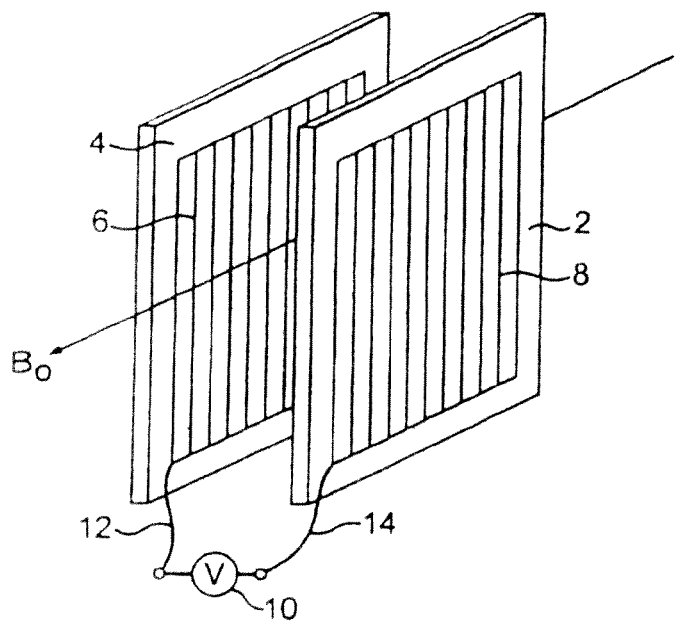
FIG. 1 represents an exemplary embodiment of breast compression paddles, each containing a parallel array of electrodes forming a Faraday shield, with the electrodes oriented perpendicular to the main magnetic field $\vec{B}_0$ of the magnetic resonance (imaging) device.

According to the present invention, a non-invasive device and method is provided to permit the measurement an/or mapping of electrical impedance, complex permittivity and complex conductivity of a sample with distributed physical properties and/or the electrical impedance of a homogeneous sample. A magnetic resonance imaging ("MRI") device can be implemented to permit the measurement of electrical impedance, complex permittivity and complex conductivity of a sample, such as a human breast. In this embodiment, measurement can be made by the application of a potential distribution across a Faraday shield device implemented with the magnetic resonance imaging device which produces a time varying electric field $\vec{E}$ in the sample, which creates a spatially distributed current field $\vec{J}$, which generates time varying focal periodic aberrations in the local magnetic field $\vec{b}_0$ that periodically vary the phase of spins within the sample. The device and method of this embodiment can thus provide the location of sample pathology for detection and both anatomic and pathological evaluation. In a homogeneous sample embodiment, a magnetic resonance device measurement can be made by the application of a potential distribution across a Faraday shield device implemented with the magnetic resonance imaging device which produces a time varying electric field in the sample, which creates a current field, which generates time varying periodic aberrations in the local magnetic field that periodically vary the phase of spins within the sample. A detection circuit is provided to yield an output that corresponds to the electrical impedance, complex permittivity and/or complex conductivity.

According to one embodiment of the present invention, the sample or object to be measured or mapped, for example a human breast, is placed within a Faraday shield device connected to a time-varying voltage source V of frequency $\Omega$ so as to produce a time varying electric field E about the Faraday shield device, where $$\breve{\vec{E}} = -\nabla \breve{V} \qquad \text{Eq. 1}$$

through Poisson's equation (in the quasi-static state)

$$\Delta \bullet (\breve{\varepsilon} \nabla \breve{V}) = \breve{\rho} \qquad \text{Eq. 2}$$

where $\breve{\varepsilon}$ is the complex permittivity and $\breve{\rho}$ is the charge distribution. This time-varying electric field creates a current distribution $\vec{J}$ in the sample or object whose intensity and phase is related to the applied electric field through the spatial distribution of the complex permittivity, complex conductivity, or electrical impedance of the sample or object. The Faraday shield device is arranged so that the current distribution in the sample being tested or object being imaged is essentially orthogonal to the main magnetic static field (present as an essential component of all magnetic resonance imaging devices as is known in the art). The time varying current field in the sample or object creates a periodic magnetic field $\vec{b}_0$ superimposed on the main magnetic field $\vec{B}_0$ and the gradient fields $\vec{G}$ which periodically varies the phase of the spins within the sample or object, inducing a line-spectrum of sideband frequencies in a receiver coil of the MRI device centered at the Larmor frequencies of the spins of the sample or object, (as is known in the art, Larmor frequencies $\omega_0$ can be made to be a function of spin location by the application of gradient fields) which sidebands are spaced by integral multiples of the phase modulating frequency $\Omega$. Each sideband amplitude and sideband temporal phase is functionally related to the known applied voltage distribution $\breve{V}$ through the complex permittivity, complex conductivity, or electric impedance distribution. The frequency at which the complex permittivity, complex conductivity, or electrical impedance distribution is mapped or measured is the frequency $\Omega$ of the periodic voltage distribution $\breve{V}$ applied to the Faraday shield device.

In an embodiment of the present invention, a breast screening application using a magnetic resonance device, a human breast is positioned in a compression device (e.g., such as that shown in FIG. 1, and described in further detail below). The MRI device can be a conventional MRI device, which provides magnetic resonance images of a sample. Example MRI devices are described in the inventor's prior U.S. Pat. Nos. 5,412,322 and 5,757,187, incorporated by reference herein in their entirety. Further, a local receiver coil or a transmitter-receiver coil (as is known in the art), can be applied directly on or near a surface of the compression device, as is further illustrated in FIG. 7. The coil should be near enough to the compression device that a signal from the tissue (e.g., breast tissue) within the compression device can be received, as known to one skilled in the art. With this configuration, or a similar variant based on the present teachings, a periodic voltage $\breve{V}$ can be continuously applied to the Faraday shield device creating a current flux distribution $\vec{J}$ in the breast producing local periodic alterations $\vec{b}_0$ in the ambient magnetic field at breast pathology sites associated with focal aberrations in complex permittivity, complex conductivity, and/or electrical impedance.

The component of the image produced by the magnetic resonance imaging device during each individual "read" period will contain spatially ordered focal aberrations marking the location of suspected pathology. According to an embodiment of the present invention, the temporal analysis of the signal received from these focal aberrations, resolved with respect to the phase of the applied voltage $\breve{V}$ produces an estimation of the relative permittivity, complex conductivity, and/or electrical impedance yielding information about the pathology present as a function of position x corresponding to the Larmor frequency $\omega_0$. Thus, the nature, extent, and distribution of pathology can be better estimated for biopsy, medical or surgical treatment, or conservative management without the use of ionizing radiation and preferably without the injection of magnetic resonance contrast agents.

FIG. 1 illustrates a compression device which includes a pair of breast compression paddles 2, 4. Incorporated on or in the paddles 2, 4 are electrode arrays 6, 8, which electrodes form a Faraday shield. According to one embodiment of the present invention, the electrode arrays 6,8 are embedded or placed within an insulating material. The insulating material preferably has a high dielectric constant and can be formed with one or more ferroelectric materials. According to an alternative embodiment of the present invention, the electrode arrays 6,8 or electrically equivalent arrays are not required to be embedded or placed within insulating material, which enables the Faraday shield device 6,8 to make electrical conductivity contact with the sample.

The parallel electrodes of the Faraday shield are oriented perpendicular to the main magnetic field $\vec{B}_0$ of the magnetic resonance (imaging) device. A purpose of the Faraday shield of the present invention is to apply a potential distribution $\breve{V}$ across the breast to be imaged or to the sample to be analyzed without significantly affecting the $B_1$ radio frequency field intrinsic to conventional magnetic resonance devices (as in known in the art). This purpose can be achieved by orienting the parallel electrodes of the Faraday shield perpendicular to the main magnetic field $B_0$ so as not to provide a conduction path either for the electric field associated with the $B_1$ radio frequency field or additionally for eddy currents resulting from the application of gradients $\vec{G}$ (intrinsic in all magnetic resonance imaging devices, as is known in the art). The electrode arrays are connected to a time varying voltage source (V) 10 of frequency $\Omega$ via connections 12 or 14 so as to produce a time varying electric field $\vec{E}$ in the object. The voltage ($\breve{V}$) can be applied continuously during the imaging sequence. Alternatively, the voltage ($\breve{V}$) can be switched on only during the "read" period. Alternatively, the voltage ($\breve{V}$) can be synchronized with the event sequence of the MRI device.

Applying a potential distribution $\breve{V}$ across the Faraday shield device creates a time varying electric field $\vec{E}$ in the sample, which creates a current distribution $\vec{J}$ in the sample or object whose local intensity and phase is related to the applied electric field through the spatial distribution of the complex permittivity, complex conductivity, or electrical impedance of the sample or object. The frequency $\Omega$ of the periodic voltage V is related to the Larmor frequency $\omega_0$ as follows: $\Omega \ll \omega_0$. Example frequency values would be apparent to one of ordinary skill in the art given the present teachings.

Figure 7:
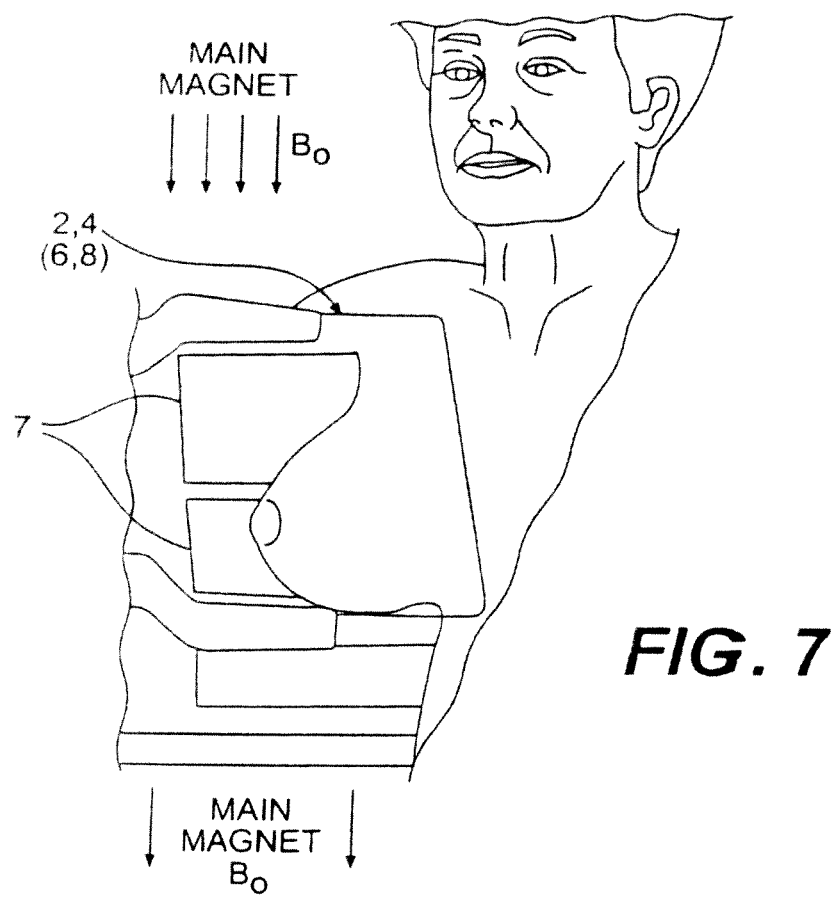
FIG. 7 shows an illustration of a magnetic resonance (imaging) device incorporating the compression device according to an embodiment of the present invention.

As an example implementation, FIG. 7 illustrates the compression of the breast by the compression paddles 2, 4 which incorporate electrodes arrays 6, 8 and a preferred position of a conventional local receiver coil or transmitter-receiver coil 7, which is preferably placed directly on or near a free surface of compression paddles 2 or 4 (as known in the art) within a conventional MRI device or system.

Using the paddles as illustrated, the current distribution $\vec{J}$ in the sample or object is essentially orthogonal to the main magnetic static field. The local time varying current field in the sample or object creates a periodic aberration in the local magnetic field, which periodically varies the phase of the spins within the sample or object, producing a line-spectrum of frequencies (see e.g., FIG. 2) in the receiver coil of the magnetic resonance (imaging) device spaced by integral multiples of the phase modulating frequency $\Omega$ about a central r.f. (Larmor) frequency $\omega_0$ corresponding to a position x.

Figure 6:
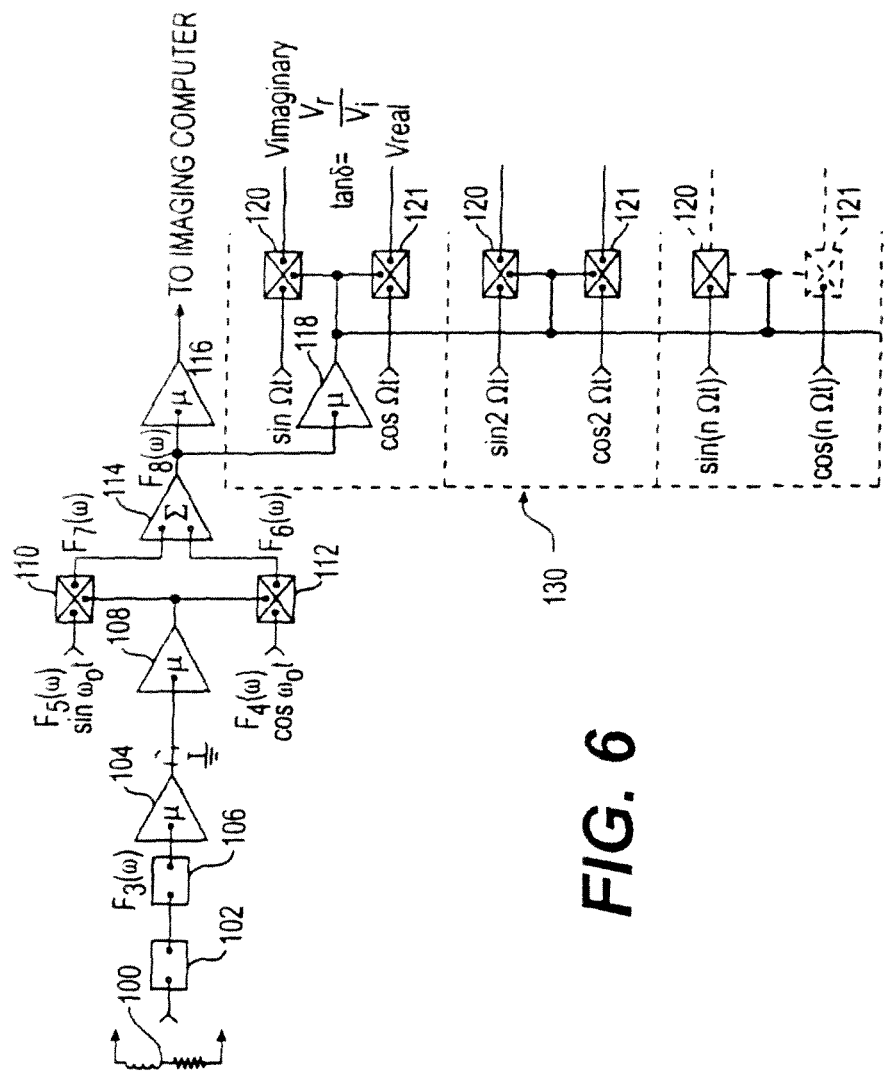
FIG. 6 represents an exemplary detector circuit 130 according to an embodiment of the invention that connects to the magnetic resonance (imaging) device for detection of the temporal orthogonal components of each sideband resolved with respect to the phase of the voltage V of frequency $\Omega$ applied to the Faraday shield device, the ratio of which sideband components yields tan $\delta$, where $\delta$ is the electric loss angle.

In particular, a detector according to an embodiment of the present invention can be used to resolve the complex permittivity, complex conductivity, and/or electrical impedance detected in the sample. An example detector/detection circuit is shown in FIG. 6. The detector measures the complex permittivity at an image location x corresponding to frequency $\omega_0'$ during the "read" portion of the acquisition sequence. Synchronous demodulators 110 and 112 can be supplied with frequency sources F4 and F5 in quadrature at frequency $\omega_0'$ and synchronous detectors 120 can be supplied with frequency sources sin ($n\Omega t$) and cos ($n\Omega t$), where $\Omega$ is the frequency of the voltage $\breve{V}$ applied to the compression paddles or electrodes. The frequency at which the complex permittivity, complex conductivity, and/or electrical impedance distribution is mapped or measured is the frequency $\Omega$ of the periodic spatially ordered voltage distribution applied to the Faraday shield device and can be variable to make measurements as a function of frequency. This detector is described in further detail below.

Figure 2A:
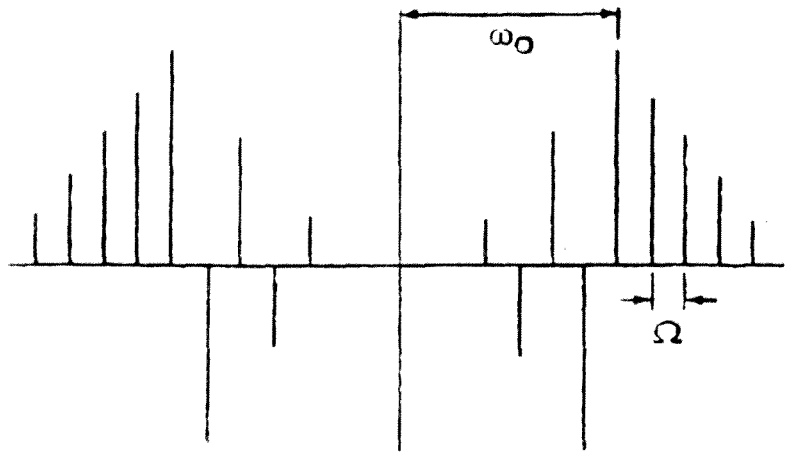
FIG. 2 represents the frequency spectrum of an isolated spin subjected to a time-varying magnetic field b of frequency $\Omega$ at position x corresponding to a Larmor frequency $\omega_0'$ in a magnetic resonance device.
Figure 2B:
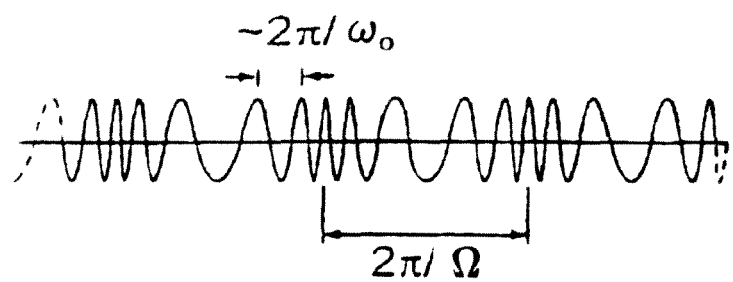

FIG. 2 represents the frequency spectrum of an isolated spin subjected to a time-varying magnetic field such as would be created at each position x corresponding to the Larmor frequency $\omega_0'$ by the time-varying magnetic field produced by the distributed current density J, $$\text{where } \omega_0' = \gamma(B_0 + Gx), \qquad \text{Eq. 3}$$

and where $\gamma$ is the gyro magnetic ratio. See e.g., FIG. 2.

Each spin then produces a voltage by magnetic induction in the receiver coil whose frequency spectrum consists of equally spaced sidebands $n\Omega$ centered at a Larmor frequency $\omega_0'$ corresponding to the location x of each spin. The amplitude of each sideband is given by:

$$J_n\left(\frac{\gamma b_0}{\Omega}\right) \qquad \text{Eq. 4}$$

The instantaneous periodic angular velocity:

$$\omega' = \gamma b \qquad \text{Eq. 5}$$

$$\text{where } b_0 = \mu h_0 \qquad \text{Eq. 6}$$

of each spin is in phase with the time-varying component of its ambient magnetic field $b_0$ which is a function of the current flux distribution J. If the current distribution is uniform, the instantaneous angular velocity of each spin will be in phase with, and the angular phase of each spin will be displaced from, the applied electric field and from the applied voltage V by the loss angle δ as would occur in a uniform sample in the measurement application. If there are focal aberrations in complex permittivity, complex conductivity, and/or electrical impedance as are associated with spatially distributed focii of breast pathology, then there will be local aberrations in the magnetic field phase and intensity, focally distorting the image produced by the conventional magnetic resonance imaging machine identifying the spatial location of pathology for further evaluation or for treatment. Analysis of the signal from these regions of distortion will produce an estimate of the complex permittivity, complex conductivity, and/or electrical impedance of the aberration which would help identify the nature of the pathology. The detector circuit 130 (see FIG. 6) according to an embodiment of the invention can measure the complex permittivity, complex conductivity, and/or electrical impedance at the phase modulating frequency Ω.

Figure 3:
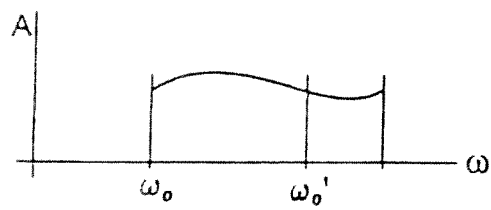
FIG. 3 represents a band spectrum produced by a clinical magnetic resonance imaging machine during the "read" time, as is known in the art.
Figure 4A:
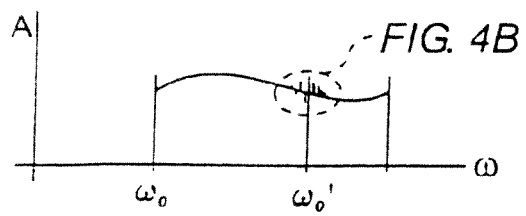
FIGS. 4A and 4B represent the superposition of FIG. 2 and FIG. 3 to produce a local aberration of signal distribution centered about frequency $\omega_0'$ which corresponds to the Larmor frequency at position x.
Figure 4B:

FIG. 3 represents the band spectrum of a frequency group produced by a clinical magnetic resonance imaging machine during the "read" time (as is known in the art). As shown in FIGS. 4A and 4B, the superposition of FIG. 3 and FIG. 2 produce a local aberration of signal distribution.

Figure 5:
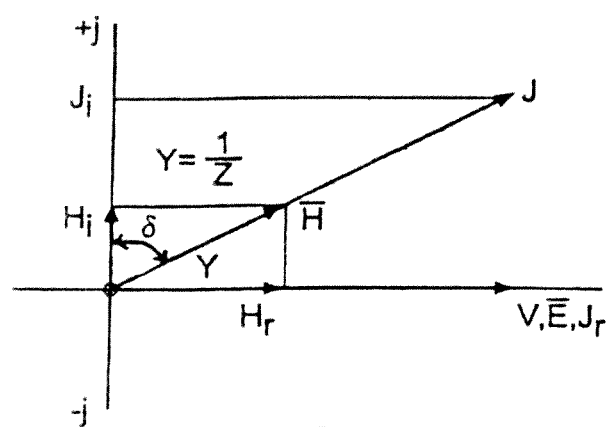
FIG. 5 represents the temporal phase relationships of the voltage $\breve{V}$ applied to the Faraday shield device, the electric field $\breve{\vec{E}}$, the local complex admittance $\breve{Y}$ or impedance $\breve{Z}$ of the breast or specimen, the local current flux density $\breve{\vec{J}}$ produced by the electric field $\breve{\vec{E}}$, the temporal orthogonal components $\vec{J}$ and $\vec{J}$ of $\breve{\vec{J}}$, the temporal orthogonal components $\vec{H}$ and $\vec{H}$ of the local magnetic field intensity $\breve{\vec{H}}$ produced by $\breve{\vec{J}}$, and the electric loss angle $\delta$ of the local complex admittance or impedance.

FIG. 5 represents the phase relationship of the voltage $\breve{V}$ of frequency Ω applied to the Faraday shield device, the electric field $\breve{\bar{E}}$ thereby created, the local complex admittance $\breve{Y}$ or impedance $\breve{\bar{Z}}$, the local current flux density $\breve{\bar{J}}$, the temporal orthogonal components $\breve{J}$ and $\breve{J}$ of $\breve{\bar{J}}$, the orthogonal components $\breve{H}$ and $\breve{H}$ of the magnetic field intensity $\breve{\bar{H}}$ produced by $\breve{\bar{J}}$, and the electric loss angle δ of the complex conductivity. Note that E corresponds to a spatial vector and $\bar{E}$ corresponds to a spatial and temporal vector.

FIG. 6 shows an exemplary detector/circuit for the demodulation of the Larmor frequency and, according to this embodiment of the present invention, for the detection of the temporal orthogonal components of each sideband of the line spectrum resolved with respect to the phase of the voltage $\breve{V}$ applied to the Faraday shield device, which yields tan δ, wherein δ is the electric loss angle. The detector provides cross-correlation with the voltage $\breve{V}$ applied to the Faraday shield for each side band. This cross correlation permits the detection of weak signals in the presence of noise. The received signal can thus be resolved as two components, one component in phase and one component 90 degrees out of phase, with the applied voltage $\breve{V}$.

Figure 8A:
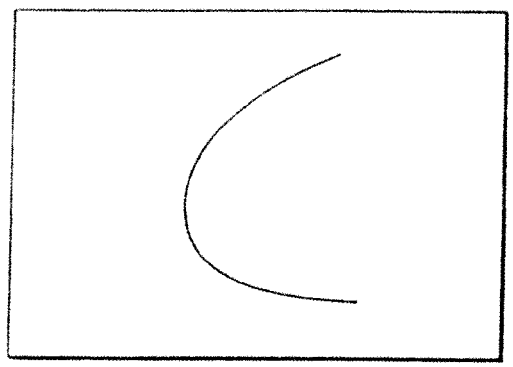
FIG. 8A, shows a first image of a breast with the Faraday shield voltage V turned off
Figure 8B:
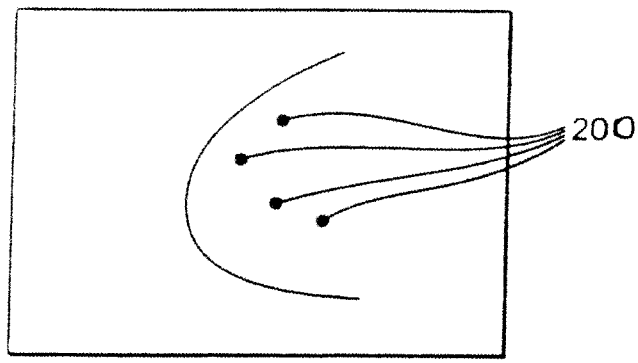

The detector of FIG. 6 can be utilized as an attachment to all magnetic resonance imaging devices for the determination of the complex permittivity, complex conductivity, and/or electrical impedance at a point x corresponding to frequency $\omega_0$. For example, as shown in FIG. 8A, a first image is of a breast with the Faraday shield voltage turned off. The second image, FIG. 8B, is an image of the same breast with the Faraday shield voltage turned on. Post processing can thus be used to measure, e.g., the complex permittivity at points of interest 200, which can be representative of local aberrations. The results at each location can be compared to values stored in look-up tables or the like as a function of frequency. Further data reduction is also contemplated, as would be apparent to one of ordinary skill in the art given the present description.

The detector of FIG. 6 can be utilized as an attachment to magnetic resonance devices for continuous homogeneous sample analysis, where δ corresponds to the electric loss angle of the sample.

The detection circuit 130 shown in FIG. 6 is shown in analogue form. As would be apparent to one of ordinary skill in the art given the present description, circuit 130 can be designed as a digital circuit. Thus, circuit 130 of FIG. 6 can be implemented as a sideband detector. The ratio of the resolved real and imaginary components of the sidebands is tangent δ, determining the electric loss angle. As is known, complex permittivity is a point function, the real component of which corresponds to the complex conductivity. When implemented in a magnetic resonance measurement device for homogeneous sample analysis, the output of circuit 130 can be calibrated to measure the total electrical impedance.

In FIG. 6, a circuit 130 according to an embodiment of the present invention is coupled at amplifier 118 to a magnetic resonance device (not fully shown for simplicity). As is known in the art, a local receiver coil 100 of the magnetic resonance machine is coupled to an impedance matching circuit 102, feeding a noise matching preamplifier 104 through a protection circuit 106. The output of the noise matching preamplifier is fed to an RF amplifier 108, the output of which is directed to a double-balanced (synchronous) demodulator 110, 112. The output of the double-balanced demodulator 110, 112 is fed through a summing amplifier 114 to an amplifier 116 and, according to this embodiment of the present invention, also to circuit 130 at amplifier 118. Each of the demodulators 110 and 112 is supplied by a quadrature output at frequency $\omega_0'$, which can be operator selected to correspond to a position x offset from the magnetic resonance master radio frequency oscillator. The demodulated outputs are then added at a summing amplifier 114 to provide input to the amplifier 116 which can feed to an imaging computer, as well as to amplifier 118 (which can be a low frequency amplifier) that, in turn, feeds additional sets of double-balanced demodulators 120, 121, each of whose cross-correlated outputs is the real or imaginary components of the signal received by the receiver coil from location x, corresponding to frequency $\omega_0'$, resolved with respect to the phase of V, the voltage applied to the Faraday shield device. The ratio of each real and imaginary signal yields the electric loss tangent δ at location x, which defines the complex permittivity at frequency Ω. The output of the detector/circuit 130 can be directed to a computer or processor ("imaging computer") for digitization and/or for calculation/display of the complex permittivity values/integrated image in accordance with the description above. In addition, the computer or processor can be continually supplied with stored values at each location for further post measurement processing and data reduction.

According to alternative embodiments, the frequency Ω can be made continuously variable yielding the electric susceptibility as a function of the frequency.

According to an alternative embodiment of the present invention, the above methodology is also applicable to electron spin resonance magnetic resonance devices for measurements at extremely high frequencies.

The invention provides several advantages. The present method and system can be used for non-invasive breast cancer screening. For example, injection of Gadolinium compounds is not required, but may be performed for supplemental imaging, as is known in the art. Further, there is no ionizing radiation. Additionally, the frequency of measurement or mapping can be varied for further analysis. Further, the signal from fatty tissue need not be suppressed, as it must be in magnetic resonance mammography.

The foregoing description of the invention has been presented for purposes of illustration and description. It is not intended to be exhaustive or to limit the invention to the precise form disclosed, and modifications and variations are possible in light of the above teachings or may be acquired from practice of the invention. The drawings and description were chosen in order to explain the principles of the invention and its practical application. It is intended that the scope of the invention be defined by the claims and their equivalents.

What is claimed is:

1. A method of detecting and evaluating sample spatially ordered pathology, comprising:
   placing an in-vivo human tissue sample to be evaluated within a magnetic resonance imaging device in proximity to a Faraday shield device, wherein the Faraday shield device comprises Faraday shields oriented so as not to significantly affect a radio frequency field generated within the magnetic resonance imaging device, and an insulating material that insulates the in-vivo human tissue sample from the Faraday shields, whereby the Faraday shield device is configured to apply a time varying potential difference to the in-vivo human tissue sample;
   applying a time varying potential difference to the Faraday shield device, so as to create a time varying electric field in the in-vivo human tissue sample and a local time varying current field in the in-vivo human tissue sample essentially orthogonal to the main magnetic field generated by the magnetic resonance imaging device which results in a periodic aberration in a local magnetic field that periodically varies a phase of spins within the in-vivo human tissue sample; and
   imaging at least one of a complex permittivity, a complex conductivity, and an electrical impedance of the in-vivo human tissue sample during the application of the time varying potential difference to the Faraday shield device.

2. The method according to claim 1, wherein the in-vivo human tissue sample is a human breast, and wherein the Faraday shield device further comprises a pair of compression paddles containing the Faraday shields oriented in parallel to each other, wherein the compression paddles substantially align with a main magnetic field of the magnetic resonance imaging device.

3. The method according to claim 2, wherein the Faraday shields comprise electrically connected substantially parallel conducting elements oriented substantially orthogonal to the main magnetic field of the magnetic resonance imaging device.

4. The method according to claim 3, wherein the compression paddles are non-conductive, the insulating material has a high dielectric constant, and the conducting elements are coupled to a voltage source that applies the time varying potential difference across the conducting elements.

5. The method according to claim 4, wherein the insulating material comprises one or more ferroelectric materials.

6. The method according to claim 3, wherein the substantially parallel conducting elements each comprises a maximum width substantially less than the length of each substantially parallel conducting element.

7. The method according to claim 6, wherein each substantially parallel conducting element is electrically insulated from each adjoining substantially parallel conducting element.

8. The method according to claim 1, further comprising:
   analyzing an image of the in-vivo human tissue sample produced by the magnetic resonance imaging device during the application of the time varying potential difference to the Faraday shield device to detect at least one of a complex permittivity, a complex conductivity, and an electrical impedance of the in-vivo human tissue sample; and
   identifying focal aberrations contained only in the image produced by the magnetic resonance imaging device and analyzed so as to locate pathology.

9. The method according to claim 1, further comprising detecting orthogonal components of each sideband of a line spectrum resolved with respect to the phase of the time varying potential difference applied to the Faraday shield device at a frequency ($\Omega$) much less than the Larmor frequency of the magnetic resonance imaging device ($\omega_0$).

10. The method according to claim 9, further comprising determining a ratio of the resolved real and imaginary components of the sidebands.

11. The method according to claim 1, wherein the in-vivo human tissue sample is a portion of a human breast.

12. The method according to claim 1, wherein the time varying potential difference is continuously applied.

13. The method according to claim 1, wherein the time varying potential is pulsed.

14. The method according to claim 1, wherein the time varying potential is timed to an event sequence of the magnetic resonance imaging device.

15. The method according to claim 1, wherein the Faraday shield device does not provide a conduction path either for the electric field associated with the radio frequency field generated within the magnetic resonance imaging device or for eddy currents resulting from the application of gradients by the magnetic resonance imaging device.

16. A system for detecting and evaluating sample pathology, comprising:
   a magnetic resonance imaging device configured to produce an image of an in-vivo human tissue sample, the magnetic resonance imaging device generating a main magnetic field and including i) a receiving coil and a transmitting coil or ii) a transmitter-receiver coil;
   a Faraday shield device comprising Faraday shields that include an insulating material that insulates the in-vivo human tissue sample from the Faraday shields oriented so as not to significantly affect a radio frequency field generated within the magnetic resonance imaging device, and electrically connected, substantially parallel conducting elements oriented substantially orthogonal to the main magnetic field of the magnetic resonance imaging device, whereby the Faraday shield device is configured to produce a time varying electric field in the in-vivo human tissue sample;
   a voltage source coupled to the conducting elements and configured to generate a periodic voltage at a frequency (1) creating a current in the in-vivo human tissue sample essentially orthogonal to the main magnetic field of the magnetic resonance device; and
   a detector configured to analyze an image of the in-vivo human tissue sample produced by the magnetic resonance imaging device to detect one of a complex permittivity, a complex conductivity, and an electrical impedance of the in-vivo human tissue sample, wherein the analyzed image is produced during production of the time varying electric field by the Faraday shield device.

17. The system according to claim 16, wherein the Faraday shield device comprises a pair of low-conductivity compression paddles containing the Faraday shields.

18. The system according to claim 16, wherein the periodic voltage is continuously applied.

19. The system according to claim 16, wherein the voltage source is pulsed.

20. The system according to claim 16, wherein the voltage source is timed to an event sequence of the magnetic resonance imaging device.

21. The system according to claim 16, wherein the in-vivo human tissue sample is a portion of a human breast.

22. The system according to claim 16, wherein the detector is configured to detect orthogonal components of each sideband of a line spectrum resolved with respect to the phase of the time varying electric field produced by the Faraday shield device at a frequency ($\Omega$) much less than the Larmor frequency of the magnetic resonance imaging device ($\omega_0$).

23. The system according to claim 22, wherein the detector is configured to determine a ratio of the resolved real and imaginary components of the sidebands.

\* \* \* \* \*